United States Patent [19]

Treddenick

[11] Patent Number: 5,192,500
[45] Date of Patent: Mar. 9, 1993

[54] FIREFIGHTER SAFETY BADGE

[76] Inventor: George A. Treddenick, 234 Kingston Row, Winnipeg, Manitoba, Canada, R2M 0T4

[21] Appl. No.: 681,005

[22] Filed: Apr. 5, 1991

[51] Int. Cl.⁵ ............................................. G01N 21/00
[52] U.S. Cl. ....................................... 422/56; 422/55; 422/58; 422/86; 422/87
[58] Field of Search ...................... 422/55, 58, 104, 83, 422/56, 86, 87

[56] References Cited

U.S. PATENT DOCUMENTS

| | | | |
|---|---|---|---|
| 3,482,944 | 12/1969 | Plantz et al. | 23/254 |
| 3,644,715 | 2/1972 | Holderith | 422/55 |
| 3,681,027 | 8/1972 | Smith | 23/232 R |
| 3,924,219 | 12/1975 | Braun | 422/83 |
| 3,990,850 | 11/1976 | Friedman et al. | 422/55 |
| 4,062,713 | 12/1977 | Anderson | 422/119 |
| 4,205,043 | 5/1980 | Esch et al. | 422/56 |
| 4,258,000 | 3/1981 | Obermayer | 422/55 |
| 4,472,353 | 9/1984 | Moore | 422/58 |
| 4,680,165 | 7/1987 | Vo-Dinh | 422/88 |
| 4,906,853 | 3/1990 | Linwood et al. | 250/551 |
| 4,913,881 | 4/1990 | Evers | 422/56 |

OTHER PUBLICATIONS

Firehouse-Dec. 1990 p. 53 by John Leahy, Jr. entitled "Tools, Techniques and Innovations".

Primary Examiner—James C. Housel
Assistant Examiner—Long V. Le
Attorney, Agent, or Firm—Adrian D. Battison; Stanley G. Ade; Murray E. Thrift

[57] ABSTRACT

A double face safety badge having indicia on its first face regarding the personal and medical history of the user, and labelled on the second face that has indicia thereon pertaining to the emergency site attended by the user. Removal of the label from the second face exposes a plurality of toxic gas indicator strips. The strips indicate to the user, or other person, an exposure to toxic gas. The label, when placed in a predetermined place, indicates the general location of a firefighter at an emergency site.

3 Claims, 1 Drawing Sheet

FIREFIGHTER SAFETY BADGE

FIELD OF THE INVENTION

The present invention is related to the field of badges, more particularly to a safety badge having thereon indicia relating to the wearer and means for the detection of harmful airborne compounds.

BACKGROUND OF THE INVENTION

The wearing of badges by people who work in a potentially hazardous environments is well known. A review of the prior art reveals a number of wearable badges or other receptacles that are used to detect potential hazards in the air near the person wearing the badge.

U.S. Pat. No. 4 205 043 (Esch) describes a badge with a hazardous gas indicator that changes color in the presence of the gas.

U.S. Pat. No. 3 482 944 (Plantz) discloses a wearable receptacle or badge that measures the presence of hazardous gas by means of a strip that changes color in the presence of a gas.

U.S. Pat. No. 4 913 881 (Evers) discloses a wearable badge again that indicates the presence of a hazardous gas or vapor. In this particular device the indicator is dosimetric and the degree of color change is determined by the extent of contamination by the gas.

U.S. Pat. No. 4 680 165 (vo-Dinh) also describes a dosimetric device that indicates the presence of organic compounds, more particularly aromatic organic compounds.

Fire fighters are often thrust into hazardous situations. When firefighters arrive at the scene of a fire they often have no idea what type of potential hazards lie ahead. There is a need for a system in which the firefighter, or other person working in a potentially hostile environment, can reduce the risk associated with their work.

The present invention addresses some of these concerns.

SUMMARY OF THE INVENTION

It is an object of the present invention therefore to provide a badge having indicia thereon to indicate the name and past medical history of the wearer, and a means for the detection and measurement of harmful gases or vapors, as well as a detachable adhesive label for placing on a surface near the scene of a fire or other emergency attended by the wearer.

It is a further object of the present invention to provide a system for the location of the firefighter at the scene of a fire or other emergency.

It is a still further object of the present invention to provide a safety badge that informs a person as to the medical history and recent exposure to harmful gas or vapor by the wearer of the device.

According to a first aspect of the present invention there is provided a safety badge for wearing by a person, comprising a badge body having a first face and a second face, means for fastening the badge body to the person with the second face thereof exposed, said second face having means defining an opening thereon, a detachable adhesive label covering the said opening and said label having indicia thereon comprising means for identifying the person, means for indicating of at least one toxic compound in an atmosphere near the said badge, said indicating means carried within the said opening on the second face, whereby removal of the detachable adhesive label exposes the said means for indicating the presence of at least one toxic compound in the atmosphere near the badge.

According to a second aspect of the present invention there is provided a method for generating records relating to a hazardous area comprising providing a badge body having thereon indicia identifying an intended user of the badge, means on the badge for indicating the presence near the badge of a toxic compound and a detachable adhesive label attached to the badge body and covering said indicating means, removing the adhesive label from the badge body to expose the indicating means to the atmosphere, applying the badge body to the person of the user for transportation by the user into a hazardous area, marking the adhesive label with indicia relating to the user and a time of entry into the hazardous area applying the label to a surface adjacent the hazardous area for collection and collecting the adhesive label and badge body to provide record of any exposure to said toxic compound by said user.

By wearing the badge and using it as described herein, the firefighter or other emergency personnel provide a means for their detection, should they go missing in an emergency situation.

The badge provides attending medical personnel with useful information regarding the potential treatment of the wearer of the badge, as well as an indication as to the nature of the environment that the wearer of the badge was in. It also provides a system for reducing the search time for a person that has gone missing, and who has employed the system properly.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of an exemplary embodiment of the present invention, in which:

DESCRIPTION OF THE DRAWINGS

In the drawings like characters of reference indicate corresponding parts in the different figures.

DETAILED DESCRIPTION

Figure 1:
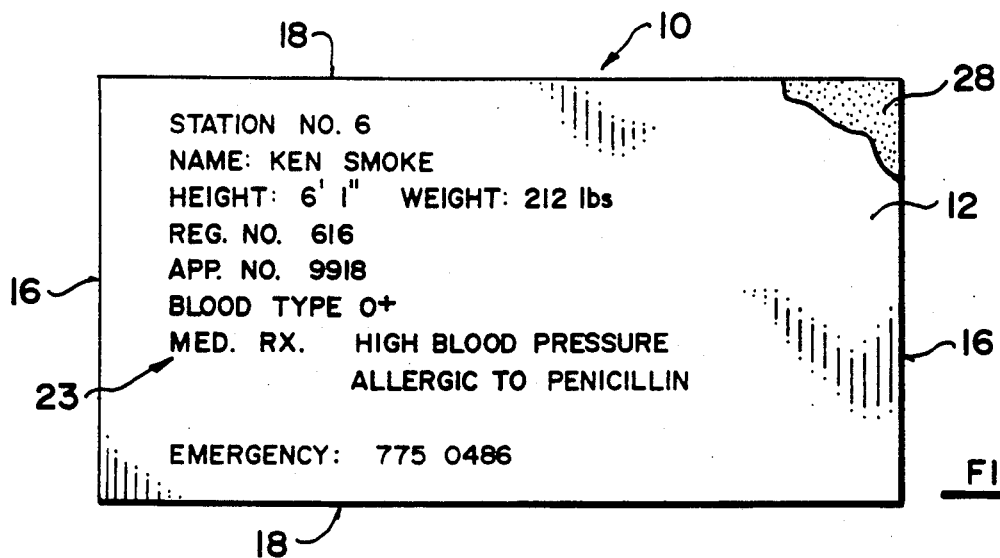
FIG. 1 is a front view of the first face of a badge according to the invention.

A safety badge is described herein in relation to its use by firefighters, however the device may be used by other emergency personnel.

With reference to the drawings, a badge is shown generally at 10. The badge is comprised of a badge body having a first face 12 and a second face 14. The faces 12 and 14 are bounded by end edges 16 and side edges 18. The second face 14 has an opening 20 thereon. The opening 20 is covered by an adhesive label 22, having a tab 24 positioned near one of the end edges 16.

Figure 2:
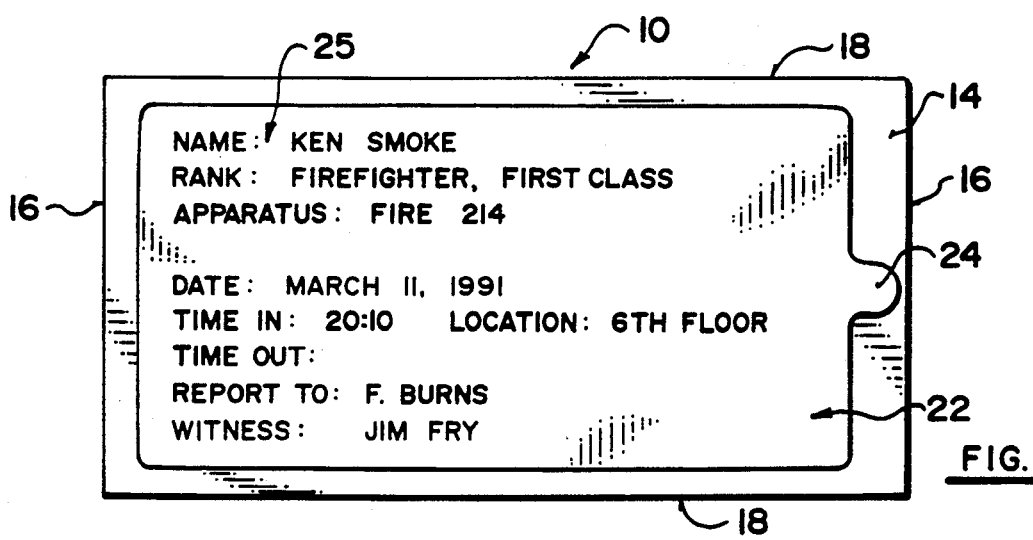
FIG. 2 is a front view of the second face of the badge of FIG. 1 with a label attached thereto.
Figure 3:
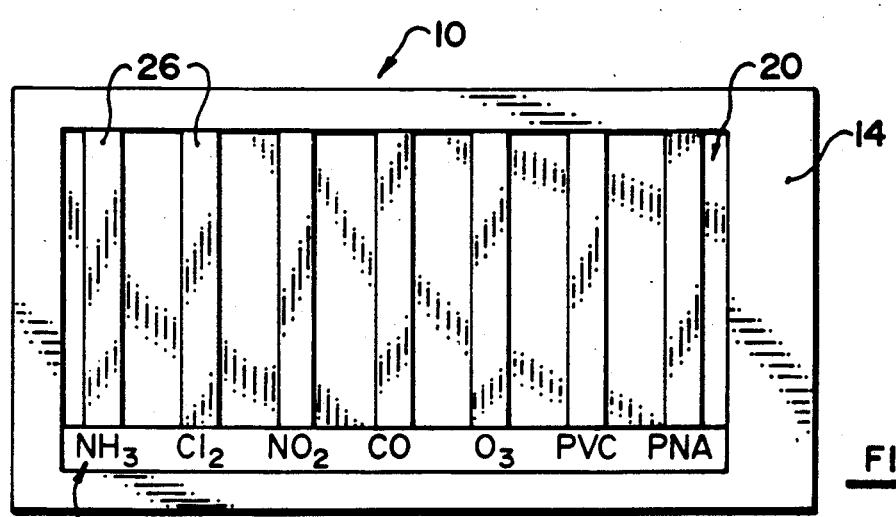
FIG. 3 is a front view of the second face of the badge of FIG. 1 with the label removed.

On the first face 12 there are indicia 23 thereon as indicated in FIG. 1. There are written pre-inked indicia 25 on the label 22 as indicated in FIG. 2 and FIG. 3. The function of the indicia written thereon is detailed below. Within the opening 20 as illustrated in FIG. 3 there are a number of indicator strips 26 that are exposed to the air only upon the removal of the label 22.

Each indicator strip 26 is labelled 27 to indicate

Each indicator strip 26 is labelled 27 to indicate what compound or group of compounds is reactive with that particular strip.

The badge 26 has a means for attachment 28 to an article of clothing worn by a firefighter. In the embodiment shown, the attachment means comprises an adhesive layer 28 carried on the rear or first face 12 which allows the badge body to be attached to the clothing of the user with the second face exposed outwardly away from the body of the user. The badge will be readily visible to another person when looking at the firefighter. In an alternative arrangement the badge may attach by way of a clip means (not shown) to an article of clothing worn by the firefighter, with face 14 facing outwardly from the firefighter. Alternatively the badge may be received in a specially provided pocket on the uniform of the user. The pocket has an opening in the front face to expose the second face of the badge.

The writing on the first face 12 of the badge, as indicated in the diagram, is pre-printed or permanent and provides the reader with personal information pertaining to the wearer of the badge such as name, badge number, height, weight, blood type, medical treatment or allergies, and emergency phone number.

The adhesive label 22 covering the opening 20 on the second face 14 of the badge provides some pre-printed information and some spaces to be filed or relating to the site of the emergency itself attended by the wearer, more specifically, name, rank, apparatus, date, time in, time out, location, reporting to, and any witnesses. Other information may also be included on either face 12 or label 22.

In operation, the firefighter coming upon an emergency situation completes the necessary information in the allotted spaces on the adhesive label 22. For example, should the firefighter be proceeding to the seventh floor of a building, he/she would indicate on the label that it is his/her location. The label 22 is removed from the badge and fastened to a surface in a predetermined location, such as a doorway or near an elevator, as determined by the type of building attended upon by the firefighters. By placing the label in one particular spot at the scene of each fire, quick reference can be made to a particular label for each firefighter at the scene to determine his/her whereabouts. The labels provide a record of who is at the scene, where they are located, and when they went to that location.

Once the adhesive label 22 has been removed, the opening 20 is exposed and the indicator strips 26 within the opening are also exposed to the surrounding atmosphere. Should the person come in contact with any harmful vapors or gases, specifically reactive with any of the pre-treated indicator strips 26, that indicator strip will indicate same by changing color. The reaction of the indicator strip may be dosimetric, in that the greater the concentration of the particular compound in the atmosphere, the greater the change in the color of the indicator strip.

For the above reasons, it is preferred that the second face of the badge be facing away from the person wearing it. Firstly, this makes it easier for the person to fill in the label and remove it. Secondly, it also allows the firefighter, or someone looking at him/her, to easily read the indicator strips 26. Also, should the face 14 be positioned against the user, the opening 20 may be covered by the body of the user, thus preventing the ambient air from contacting the strips 26 and preventing their specific reactions. This would result in an inaccurate indication of the presence of harmful gas or vapors.

Should a firefighter be found incapacitated for whatever reason, the attending medical personnel will have important information regarding the individual's medical history, as well as an indication of his/her recent exposure to harmful fumes, if the device is used properly. This information may determine the best course of medical treatment for the person.

It is expected that the person in charge of the emergency operation, or another designated person, will monitor the labels to determine the location of the firefighters, and use this information in conjunction with incoming reports regarding the emergency situation.

In the embodiment described, the indicator strips are not re-usable and they are collected and claimed as records once the emergency situation has ended. There are a number of companies that provide specific indicator strips that react with unusually high concentrations of such potentially hazardous substances commonly found at fire sites such as ammonia, chlorine, hydrogen sulfide, nitrogen dioxide, ozone, carbon monoxide, hydrazine, polyvinylchlorides and polynuclear aromatic compounds. This list is not meant to be inclusive and other indicator strips may be used for measuring other compounds.

The removed label and the indicator strip are then collected and retained as a permanent record of the exposure of the user to the toxic chemicals. The main badge body will be retained by the user for future use by replacement of the indicator strip, attachment of a fresh adhesive label and re-attachment of the badge body to the clothing of the wearer.

Since various modifications can be made in my invention as hereinabove described, and many apparently widely different embodiments of same made within the spirit and scope, it is intended that all matter contained in the accompanying specification shall be interpreted as illustrative only and not in a limiting sense.

I claim:

1. A method for generating records relating to the entry into a hazardous area of a person comprising providing a badge body having thereon indicia identifying and relating to the person intended to use the badge body, providing on the badge body means for indicating the presence near the badge of a toxic compound, providing a detachable adhesive label attached to the badge body and covering said indicating means, providing on an exposed surface of the adhesive label indicia identifying the person and providing blank areas arranged for manual entry of further indicia relating to a time of entry into the hazardous area and identifying the hazardous area, prior to entering the hazardous area, manually marking the adhesive label with said indicia relating to the hazardous area and a time of entry into the hazardous area, removing the adhesive label from the badge body to expose the indicating means to the atmosphere, attaching the badge body to the person for transportation by the person into a hazardous area, attaching the marked label to a surface adjacent the hazardous area for collection, and subsequently collecting the adhesive label and badge body to provide record of any exposure to said toxic compound by said person.

2. The method according to claim 1 wherein the indicia on the badge body are applied thereto as a substantially permanent record.

3. The method according to claim 1 wherein the indicia on the badge body includes medical information concerning said person.

* * * * *